United States Patent
Park et al.

(10) Patent No.: US 10,794,942 B2
(45) Date of Patent: Oct. 6, 2020

(54) APPARATUS AND METHOD FOR PROCESSING SPECTRUM

(71) Applicant: SAMSUNG ELECTRONICS CO., LTD., Suwon-si (KR)

(72) Inventors: Yun S Park, Suwon-si (KR); Sung Mo Ahn, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 197 days.

(21) Appl. No.: 15/891,484

(22) Filed: Feb. 8, 2018

(65) Prior Publication Data

US 2019/0128934 A1 May 2, 2019

(30) Foreign Application Priority Data

Oct. 31, 2017 (KR) .................. 10-2017-0144144

(51) Int. Cl.
| | |
|---|---|
| *A61B 5/1455* | (2006.01) |
| *G01R 23/163* | (2006.01) |
| *G01R 23/17* | (2006.01) |
| *G01R 23/18* | (2006.01) |
| *G01N 21/65* | (2006.01) |

(Continued)

(52) U.S. Cl.
CPC .......... *G01R 23/163* (2013.01); *A61B 5/0075* (2013.01); *A61B 5/7225* (2013.01); *G01J 3/027* (2013.01); *G01R 23/17* (2013.01); *G01R 23/18* (2013.01); *A61B 5/0022* (2013.01); *A61B 5/021* (2013.01); *A61B 5/14532* (2013.01); *A61B 5/6824* (2013.01); *A61B 5/6826* (2013.01); *A61B 2560/0209* (2013.01); *G01J 3/18* (2013.01); *G01J 3/44* (2013.01); *G01J 2003/1213* (2013.01); *G01N 21/65* (2013.01)

(58) Field of Classification Search
None
See application file for complete search history.

(56) References Cited

U.S. PATENT DOCUMENTS

| | | |
|---|---|---|
| 5,457,501 A | 10/1995 | Hong |
| 6,574,501 B2 | 6/2003 | Lambert et al. |

(Continued)

FOREIGN PATENT DOCUMENTS

| | | |
|---|---|---|
| KR | 1019930022909 A | 11/1993 |
| KR | 100354958 B1 | 10/2002 |

(Continued)

OTHER PUBLICATIONS

Yvan Saeys et al., "A review of feature selection techniques in bioinformatics", Bioinformatics vol. 23, No. 19, 2007 (pp. 2507-2517).

(Continued)

*Primary Examiner* — Eric F Winakur
*Assistant Examiner* — Marjan Fardanesh
(74) *Attorney, Agent, or Firm* — Sughrue Mion, PLLC

(57) ABSTRACT

A spectrum processing apparatus includes: a spectrum obtainer configured to obtain an optical spectrum from a light that is scattered or reflected from a subject; and a processor configured to split the optical spectrum into a plurality of bands, determine, based on a predetermined measurement accuracy for measuring a biosignal from the light, one or more key bands from the plurality of bands, and obtain the biosignal from the determined key bands.

18 Claims, 12 Drawing Sheets

(51) Int. Cl.
*A61B 5/00* (2006.01)
*G01J 3/02* (2006.01)
*A61B 5/021* (2006.01)
*G01J 3/12* (2006.01)
*G01J 3/18* (2006.01)
*A61B 5/145* (2006.01)
*G01J 3/44* (2006.01)

(56) References Cited

U.S. PATENT DOCUMENTS

| | | |
|---|---|---|
| 7,303,922 B2 | 12/2007 | Jeng et al. |
| 8,260,402 B2 | 9/2012 | Ermakov et al. |
| 8,326,404 B2 | 12/2012 | Zeng et al. |
| 9,599,510 B2 | 3/2017 | Duffey et al. |
| 2005/0123917 A1 | 6/2005 | Labischinski et al. |
| 2006/0063993 A1 | 3/2006 | Yu et al. |
| 2010/0079753 A1 | 4/2010 | Hehlen |
| 2011/0184654 A1 | 7/2011 | Ben-David et al. |
| 2013/0035568 A1* | 2/2013 | Toriumi ............... A61B 5/1455 600/322 |
| 2016/0256116 A1 | 9/2016 | Baik et al. |

FOREIGN PATENT DOCUMENTS

| | | |
|---|---|---|
| KR | 100358113 B1 | 10/2002 |
| KR | 100842827 B1 | 7/2008 |
| KR | 101094763 A | 12/2011 |
| KR | 1020160108081 A | 9/2016 |

OTHER PUBLICATIONS

Isabelle Guyon et al., "An Introduction to Variable and Feature Selection", Journal of Machine Learning Research 3, 2003 (pp. 1157-1182).

Harvey Lui et al., "Real-Time Raman Spectroscopy for In Vivo Skin Cancer Diagnosis", Cancer Research; 72(10), Mar. 20, 2012 (11 total pages).

Igor V. Ermakov et al., "Resonance Raman detection of carotenoid antioxidants in living human tissue", J. Biomed Opt. NIH Public Access Author Manuscript 2005; 10(6 (pp. 1-35).

Narahara Chari Dingari et al., "Investigation of the specificity of Raman spectroscopy in non-invasive blood glucose measurements", Anal Bioanal Chem. NIH Public Access Author Manuscript, 400 (9), Jul. 2011, (18 pages total).

* cited by examiner

APPARATUS AND METHOD FOR PROCESSING SPECTRUM

CROSS-REFERENCE TO RELATED APPLICATION(S)

This application claims priority from Korean Patent Application No. 10-2017-0144144, filed on 31 Oct. 2017 in the Korean Intellectual Property Office, the disclosure of which is incorporated herein by reference in its entirety.

BACKGROUND

1. Field

Apparatuses and methods consistent with exemplary embodiments relate to processing spectrum data.

2. Description of the Related Art

Commonly used Raman spectroscopy applications use the Raman spectral band that is unnecessarily wide and has an unnecessarily high resolution, such that it is difficult to make an apparatus using the Raman spectroscopy in a smaller size.

That is, in order to use the unnecessarily wide Raman spectral band, a detecting stage using a plurality of band-pass filters is required, and in order to maintain the unnecessarily high resolution, a signal to noise ratio (SNR) is reduced due to a reduced light amount, and a spectrometer may not be realized in a small size due to physical limitations.

Accordingly, research is being conducted on a small spectrometer which may be mounted in a small device, such as a wearable device, a mobile device, or a small spectrometer.

SUMMARY

According to an aspect of an exemplary embodiment, there is provided a spectrum processing apparatus, including: a spectrum obtainer configured to obtain an optical spectrum from a light that is scattered or reflected from a subject; and a processor configured to split the optical spectrum into a plurality of bands, determine, based on a predetermined measurement accuracy for measuring a biosignal from the light, one or more key bands from the plurality of bands, and obtain the biosignal from the determined key bands.

The processor may be further configured to determine the key bands based on at least one of a type of a measurement object, a measurement position of the subject, an age group to which the subject belongs, a gender group to which the subject belongs, and a computing power of a bio-information measurement apparatus including the spectrometer.

The processor may be further configured to determine a number of the key bands to be selected from the plurality of bands by selecting bands from the plurality of bands while varying a number of the selected bands, and by repeatedly performing performance evaluation of the spectrometer by using the selected bands.

The processor may be further configured to determine a rank of each of the plurality of bands, and determine, among the plurality of bands, a number of candidate bands to be changed by performing forward selection on one or more of the plurality of bands having a rank higher than a first predetermined rank, based on the determined rank of each of the plurality of bands.

The processor may be further configured to determine the rank of each of the plurality of bands based on Random Forest Regression.

The processor may be further configured to determine the number of candidate bands to be changed, by determining the rank of each of the plurality of bands according to a correlation between the plurality of bands, and by performing backward elimination on one or more of the plurality of bands having a rank lower than a second predetermined rank.

The processor may be further configured to determine the rank of each of the plurality of bands based on Partial Least Square Regression.

Upon determining the key bands, the processor may determine a resolution of the spectrometer that satisfies the predetermined measurement accuracy by adjusting a resolution for the determined key bands.

The apparatus may further include a communicator configured to obtain a spectrum from an external spectrum detection apparatus.

The optical spectrum may be a Raman spectrum.

According to an aspect of an exemplary embodiment, there is provided a spectrum processing method, including: obtaining an optical spectrum from a light that is scattered or reflected from a subject; splitting the optical spectrum into a plurality of bands; determining one or more key bands from the plurality of bands based on a predetermined measurement accuracy for measuring a biosignal from the light; and obtaining the biosignal from the determined key bands.

The determining one or more key bands may include determining the one or more key bands further based on at least one of a type of a measurement object, a measurement position of the subject, an age group to which the subject belongs, a gender group to which the subject belongs, and a computing power of a spectrometer that performs the spectrum processing method.

The determining the key bands may include: selecting a predetermined number of candidate bands from the plurality of bands; evaluating performance of a spectrometer that performs the spectrum processing method by using the selected candidate bands; determining whether a result of evaluating the spectrometer satisfies the predetermined measurement accuracy; in response to the result of evaluating the performance of the spectrometer satisfying the predetermined measurement accuracy, changing the predetermined number of candidate bands and selecting the candidate bands as the key bands; and in response to the result of evaluating the performance of the spectrometer not satisfying the predetermined measurement accuracy, determining the predetermined number of candidate bands to be the key bands.

The selecting the candidate bands may include: determining a rank of each of the plurality of bands; and determining, among the plurality of bands, a number of the candidate bands to be changed by performing forward selection on one or more of the plurality of bands having a rank higher than a first predetermined rank based on the determined rank of each of the plurality of bands.

The determining the rank of each of the plurality of bands may include determining the rank based on Random Forest Regression.

The selecting the candidate bands may include: determining a rank of each of the plurality of bands according to a correlation between the plurality of bands; and determining a number of the candidate bands to be changed by performing backward elimination on one or more of the plurality of bands having a rank lower than a second predetermined rank based on the determined rank of each of the plurality of bands.

The determining the rank of each of the plurality of bands may include determining the rank based on Partial Least Square Regression.

The method may be performed by a spectrometer, and the method may further include, upon determining the key bands, determining a resolution of the spectrometer that satisfies the predetermined measurement accuracy by using the determined key bands.

The determining the resolution may include: setting a resolution for the determined key bands; evaluating performance of the spectrometer based on the set resolution; in response to a result of evaluating the performance of the spectrometer satisfying the predetermined measurement accuracy, adjusting the resolution for the determined key bands and evaluating the performance of the spectrometer; and in response to a result of evaluating the performance of the spectrometer not satisfying the predetermined measurement accuracy, determining the resolution that is set for the determined key bands before adjustment, to be the resolution of the spectrometer.

The obtaining the optical spectrum may include obtaining the optical spectrum from an external spectrum detection apparatus through a communication module.

BRIEF DESCRIPTION OF THE DRAWINGS

The above and/or other aspects will be more apparent by describing certain exemplary embodiments, with reference to the accompanying drawings, in which.

DETAILED DESCRIPTION

Figure 1:
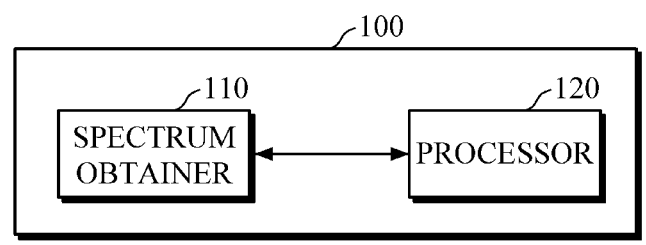
FIG. 1 is a block diagram illustrating a spectrum processing apparatus according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

It will be understood that, although the terms first, second, etc. may be used herein to describe various elements, these elements should not be limited by these terms. These terms are only used to distinguish one element from another. Any references to singular may include plural unless expressly stated otherwise.

In addition, unless explicitly described to the contrary, an expression such as "comprising" or "including" will be understood to imply the inclusion of stated elements but not the exclusion of any other elements. Also, the terms, such as 'part', 'unit' or 'module' etc. should be understood as a unit that performs at least one function or operation and that may be embodied as hardware, software, or a combination thereof.

Expressions such as "at least one of," when preceding a list of elements, modify the entire list of elements and do not modify the individual elements of the list.

FIG. 1 is a block diagram illustrating an example of a spectrum processing apparatus.

Referring to FIG. 1, the spectrum processing apparatus 100 includes a spectrum obtainer 110 and a processor 120. Here, the processor 120 may include one or more processors, a memory, and a combination thereof.

The spectrum obtainer 110 may obtain an optical spectrum from a light reflected or scattered by a target object.

For example, the spectrum obtainer 110 may include one or more light sources and a detector, and the spectrum may be a Raman spectrum that is obtained from scattered light which is generated when light is emitted from a light source and collides with atoms or molecules in an object.

However, the spectrum is not limited thereto, and the spectrum obtainer 110 may obtain an absorption spectrum, a transmission spectrum, or a reflected spectrum, which is measured by emitting near-infrared light or mid-infrared light onto an object.

Further, the spectrum obtainer 110 may transmit or receive spectrum data to and from an external device by communicating with the external device. For example, the spectrum obtainer 110 may transmit or receive spectrum data to and from the external device by using Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, and the like.

Examples of the electronic device may include a cellular phone, a smartphone, a tablet PC, a laptop computer, a personal digital assistant (PDA), a portable multimedia player (PMP), a navigation, an MP3 player, a digital camera, a wearable device, and the like, and may also be a spectrometer mounted in these devices. However, the electronic device is not limited to the above examples, and may be various devices that store spectrum data, or may be an external spectrum obtaining device.

The processor 120 may split the obtained spectrum into one or more wavelength bands. A unit of a wavelength band that divides the spectrum may be referred to "wavelength band unit" or "band unit." The band unit may indicate a range wavelengths (e.g., 1 nm), and each band unit may have the same size (e.g., 1 nm).

Figure 2:
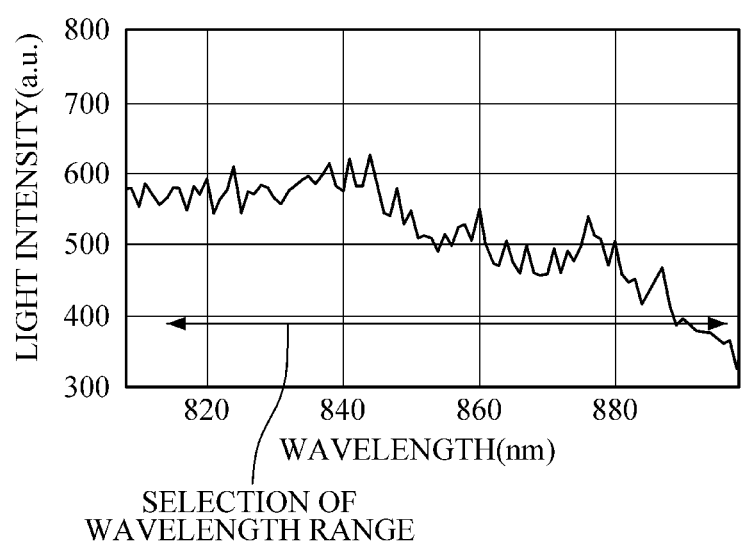
FIG. 2 illustrates an example of splitting a unit spectrum according to an exemplary embodiment.

FIG. 2 illustrates an example of splitting an optical spectrum into a plurality of spectrum units. Hereinafter, referring to FIGS. 1 and 2, the processor 120 may split the obtained spectrum into a plurality of wavelength band units.

The processor 120 may split all the regions of the obtained spectrum into a plurality of wavelength band units. Further, the processor 120 may select a specific wavelength range required for spectrum analysis, and may split the spectrum in the selected specific wavelength range into band units.

For example, the processor 120 may split the obtained spectrum in a minimum unit of wavelength (e.g., 1 nm). For example, the processor 120 may split the wavelength range of 809 nm to 899 nm the obtained spectrum the unit of 1 nm, thereby splitting the spectrum into 91 band units.

In another example, the processor 120 may split the obtained spectrum into band units by adjusting the minimum unit of wavelength. For example, by determining the minimum wavelength unit to be 2 nm, the processor 120 may split the spectrum into band units, thereby splitting the wavelength range of 809 nm to 899 nm of the spectrum into 45 band units.

The processor 120 may determine one or more key bands, which satisfy a measurement condition, to optimize a spectrometer.

Here the measurement condition may be predetermined according to at least one of a type of a measurement object, measurement accuracy, a measurement position of a spectrum, a user group, computing power of a processor, and specifications of a measurement apparatus. The measurement condition may be determined according to the purpose of use and intention of the spectrum processing apparatus 100.

The type of a measurement object may indicate a sample of the obtained spectrum, and may be, for example, blood glucose, protein, lipid, skin components, an antioxidant level, and the like, as biological components of a human body; and may include various objects which may be used for spectrum analysis such as qualitative and quantitative analysis of fine dust.

Further, the measurement accuracy may indicate accuracy of information to be analyzed and estimated in the obtained spectrum information, and may include a similarity evaluation index such as a coefficient of correlation between a ground truth for a measurement object and an estimated value which is estimated from the spectrum. Further, the measurement accuracy may be changed in connection with other measurement conditions.

For example, the measurement accuracy may be changed according to the types of measurement objects, and in the case where a measurement object is blood glucose, the measurement accuracy may include a coefficient of correlation, which is determined to be equal to or higher than 0.6, between a blood pressure value estimated from a spectrum and a ground truth.

Further, the measurement position of a spectrum may indicate a position of a measurement object where the spectrum is measured. For example, in the case where a spectrum is obtained from human skin, the thickness and components of the skin may be different depending on measurement positions. In this case, the measurement position may indicate a position, such as a finger, a wrist, an upper arm, and a back of a hand, where a spectrum is measured.

Further, the user group indicates a group which uses the spectrum measurement apparatus, and may be classified according to, for example, a user's occupation, age, gender, weight, and purpose of use of the spectrum measurement apparatus.

Further, the computing power of the bio-information measurement apparatus including a spectrometer indicates computing power of the measurement apparatus using a key band, which is determined from the obtained spectrum, and an optimal resolution; and may indicate, for example, the computing power of a wearable device in the case of a small wearable device using the key band determined by the spectrum processing apparatus 100.

Further, the specifications of the measurement apparatus indicate specifications of the measurement apparatus using the key band determined based on the obtained spectrum, and may indicate, for example, a spectrometer, a wearable device, or a mobile device using the key band determined by the spectrum processing apparatus 100. In this case, the specifications may indicate the size, purpose of use, power consumption, a target for use, and the like, of a measurement apparatus, in order to avoid unnecessary increase in size, power consumption, and computation of device.

Such measurement condition may be set independently from each other, and may be dependent on other measurement conditions. Further, the measurement condition may be set by a user though an input part of the spectrum processing apparatus 100, which will be described later.

Further, the processor 120 may determine one of a plurality of band units as a key band unit according to predetermined measurement conditions as described above.

For example, the processor 120 may select band units from among the plurality of band units while varying the number of band units, and may repeatedly perform performance evaluation of a spectrometer by using the selected band units; and may determine, as key bands, a predetermined number of band units which satisfy the performance evaluation of the spectrometer.

Here, the performance evaluation of the spectrometer may indicate a process of evaluating measurement accuracy of a measurement object. However, the performance evaluation of the spectrometer is not limited thereto, and may vary according to predetermined measurement conditions.

The processor 120 may perform a stepwise regression method to select and evaluate band units. The stepwise regression method may include a forward selection and a backward elimination. For example, the processor 120 may select band units from among the band units, which are obtained by splitting the obtained spectrum, while varying the number of band units, and may repeatedly perform performance evaluation of a spectrometer by using the selected band units.

For example, in the case of splitting the wavelength range of 809 nm to 899 nm of the obtained spectrum into 91 band units, each unit having the unit size of 1 nm, the processor 120 may perform performance evaluation by selecting the 91 band units, and recording the evaluation, and then may perform performance evaluation again by selecting 90 band units among the 91 band units and recording the evaluation. In this manner, the processor 120 may repeatedly perform performance evaluation while varying the number of band units until the processor 120 selects the last band unit and performs the performance evaluation.

Based on the performance evaluation of the spectrometer, the processor 120 may determine, as key bands, a predetermined number of band units which satisfy a measurement condition.

For example, in the case where the types of bio-information measurement objects are different, the number of band units that satisfy a measurement condition may be determined differently. For example, in the case of diagnosing skin cancer by analyzing skin components using Raman spectroscopy, it may be required to place a higher importance on the accuracy of diagnosis than on the speed of diagnosis. In this case, the processor 120 may determine all the band units to be key bands.

Further, in the case of measuring blood glucose by using a spectrometer mounted in a wearable device or a mobile device, measurement may be performed rapidly, but reliability of the estimated blood glucose value may be required to be equal to or higher than a predetermined level. In this case, the processor 120 may determine the key bands, which are to be used for measuring blood glucose by the spectrometer mounted in a wearable device or a mobile device, by determining a point of a trade-off between the speed and accuracy of measurement. The method of selecting the key bands based on a trade-off with performance will be described later.

In another example, in the case where the bio-information measurement apparatus including a spectrometer is a wearable device, a small bio-information measurement device, or a mobile device, the computing performance may be lower than a large spectrometer for medical use or for use in the precise diagnosis. In this case, the processor 120 may determine only 10% of all the band units to be key bands.

In yet another example, in the case of using the key bands determined by the spectrum processing apparatus 100 for a spectrometer included in a small device such as a wearable device and/or a mobile terminal, the processor 120 may determine, as key bands, only the band units corresponding to a point of trade-off between performance and the number of key bands based on the size, computation amount, and power consumption of a device.

In another example, the processor 120 may determine one or more band units to be key bands based on measurement accuracy. For example, upon selecting some band units from among a plurality of band units, the processor 120 may calculate an estimated value of a measurement object, and may calculate a coefficient of correlation between the calculated estimated value and a ground truth for the measurement object.

In this case, the processor 120 may repeatedly calculate the coefficient of correlation by selecting different numbers of band units, and the processor 120 may determine, as key bands, a minimum number of band units that may maintain the coefficient of correlation to be equal to or greater than a predetermined value.

In this manner, the spectrum processing apparatus 100 may determine, as key bands, some band units among the plurality of band units according to measurement conditions.

Figure 3A:
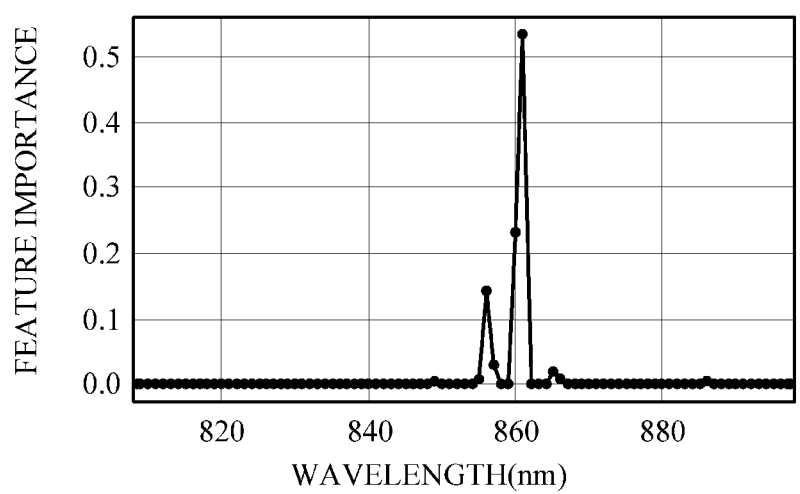
FIGS. 3A and 3B are graphs explaining an example of determining key bands.
Figure 3B:
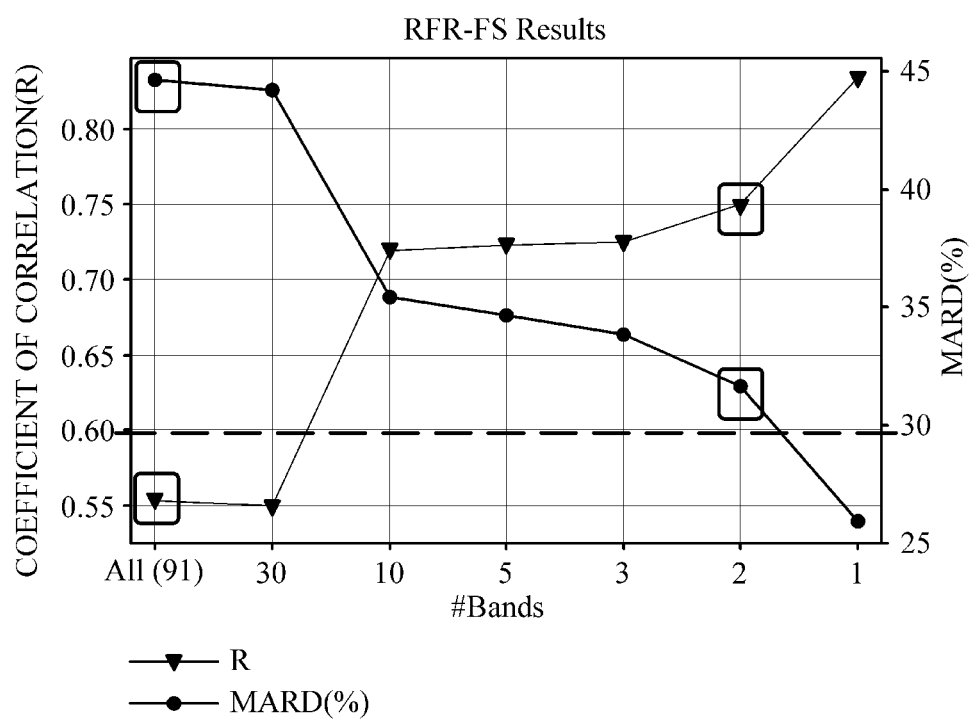

FIGS. 3A and 3B are exemplary diagrams explaining an example of determining key bands.

Referring to FIGS. 1 and 3A, the processor 120 may extract features of band units, and may determine a rank of each band unit according to feature importance of each band unit.

For example, FIG. 3A illustrates a result of calculation of feature importance by extracting features of the band units which are obtained by splitting, in the unit of 1 nm, a Raman spectrum having a wavelength range of 809 nm to 899 nm obtained for estimation of blood pressure, in which importance is converged in the wavelength regions of 856 nm and 861 nm.

In this case, the processor 120 may determine the rank of each band unit in order of the calculated feature importance.

The processor 120 may determine key bands by forward selection of one or more band units based on the determined rank of each unit band. For example, the processor 120 may determine the number of band units to be changed by determining the rank of each band unit according to the importance of band units, and by forward selection of band units which are ranked high based on the determined rank of each unit band.

For example, FIG. 3B illustrates a coefficient of correlation between an actual blood pressure value and an estimated blood pressure value, and a change in Mean Absolute Relative Difference (MARD), which are calculated by selecting band units in the wavelength regions of 856 nm and 861 nm, in which importance is converged, by using Random Forest Regression (RFR), and by varying the number of all the band units in the wavelength regions until one band unit remains.

With reference to FIGS. 1 and 3B, the processor 120 may select the band units in the wavelength region of 861 nm, having the highest importance value, by forward selection of the band units in order of 91, 90, 89, . . . , 2, and 1 in order of higher rank, and may calculate the coefficient of correlation between a ground truth and an estimation result, and a change in MARD based on the selected band units.

As shown in FIG. 3B, based on an estimation result of blood pressure obtained by determining all the band units to be key bands, the coefficient of correlation exceeds 0.8, and the MARD is estimated to be about 25%, such that reliability of the blood pressure value is very high.

However, using all the band units may lead to unnecessary increase in the computation amount, and requires large equipment since in all the wavelength regions of a spectrum should be used.

Accordingly, the processor 120 may determine a trade-off between the performance and size of a spectrometer and reliability of an estimated value.

For example, referring to FIG. 3B, in the case of using two band units in the wavelength regions of 860 nm and 861 nm in which the feature importance is converged, the coefficient of correlation is about 0.63, and the MARD is about 31%, such that estimation data is highly reliable, and the number of band units required to be computed is significantly reduced from 91 to 2, thereby obtaining high gain in performance and size in contrast to reduced reliability. Accordingly, by determining the band units in two wavelength regions of 860 nm and 861 nm to be key bands, a trade-off between performance, size, and reliability may be obtained, such that the processor 120 may determine the two band units to be key bands.

Here, for convenience of explanation, the above description is made by using an example of selecting the band units in a higher rank and calculating a correlation between a ground truth and an estimation result by gradually reducing the number of band units. However, the present disclosure is not limited thereto, and a correlation coefficient and MARD may be calculated by first selecting a band unit having the highest importance value, and by sequentially adding a band unit in a next rank repeatedly until no band unit remains to be added.

In another example, the processor 120 may determine key bands by backward elimination of one or more band units based on the determined rank of each unit band. For example, the processor 120 may determine the rank of each band unit based on a correlation between the band units, and may determine the number of band units to be changed by backward elimination of band units in a lower rank.

Figure 4:
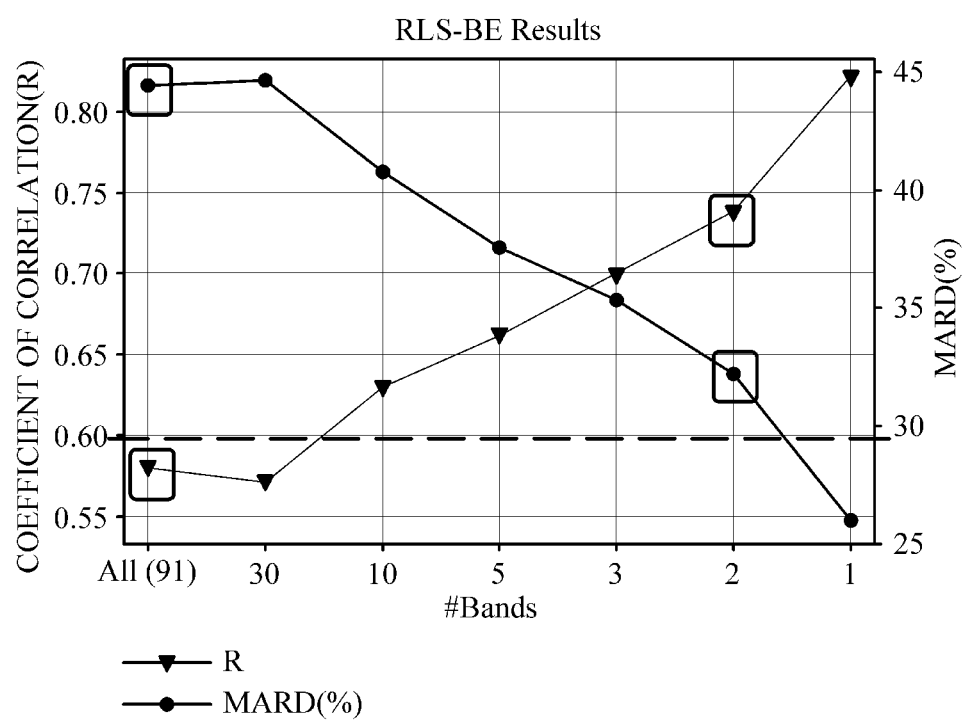
FIG. 4 is a graph explaining another example of determining key bands.

FIG. 4 is an exemplary diagram explaining another example of determining key bands.

Referring to FIGS. 1 and 4, FIG. 4 illustrates a coefficient of correlation between an actual blood pressure value, which is obtained by backward elimination by using a partial least square regression (PLSR), and an estimated blood pressure value which is estimated from key bands determined by using the selected band units, and a change in Mean Absolute Relative Difference (MARD).

That is, the processor 120 may determine the rank of each band unit in order of the size of coefficient of correlation by calculating the correlation between all the band units, and may re-calculate the correlation by eliminating band units in a lower rank one by one.

The processor 120 may calculate the rank of each band unit based on the correlation between 91 band units to eliminate a band unit having the lowest correlation with other band units, and may re-calculate the rank of 90 band units. In this manner, the processor 120 may sequentially eliminate band units in a lower rank, and may repeat the process until no band unit remains to be eliminated.

Referring back to FIG. 4, in the case of backward elimination by using all the 91 band units, the coefficient of correlation exceeds 0.8, and the MARD is about 43%, such that reliability of estimation data (e.g., blood pressure) is very high.

However, using all the band units may lead to unnecessary increase in the computation amount, and requires large equipment since in all the wavelength regions of a Raman spectrum should be used.

Accordingly, the processor 120 may determine a trade-off between performance, size, and reliability.

For example, referring to FIG. 4, in the case of using two band units in the wavelength regions of 860 nm and 861 nm among all the band units, the coefficient of correlation is about 0.63, and the MARD is about 33%, such that estimation data is highly reliable, and the number of band units to be computed is significantly reduced from 91 to 2, thereby obtaining high gain in performance and size in contrast to reduced reliability.

Accordingly, by determining, as key bands, the band units in two wavelength regions of 860 nm and 861 nm having the highest correlation, a trade-off between performance, size, and reliability may be obtained, such that the processor 120 may determine the two band units to be key bands.

The processor 120 may determine an optimal resolution of a spectrometer, which satisfies measurement conditions, while adjusting a resolution for the determined key bands.

Here, the optimal resolution may be a resolution of a spectrometer that satisfies a measurement condition, and may be a minimum resolution for the key bands determined according to the measurement condition.

Figure 5A:
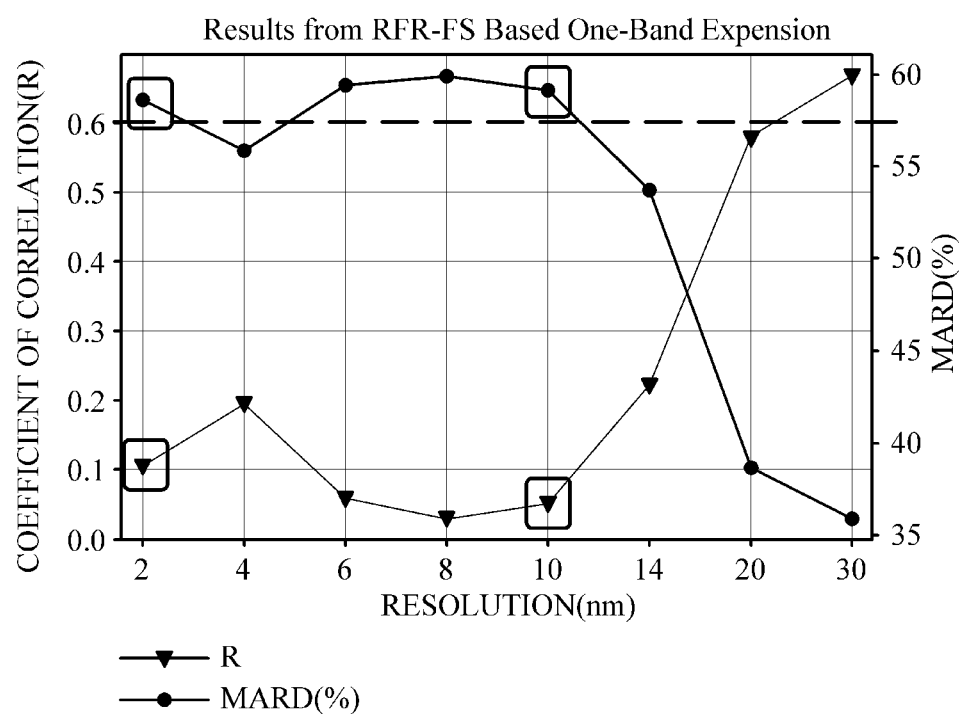
FIGS. 5A and 5B are graphs explaining an example of determining an optimal resolution.
Figure 5B:
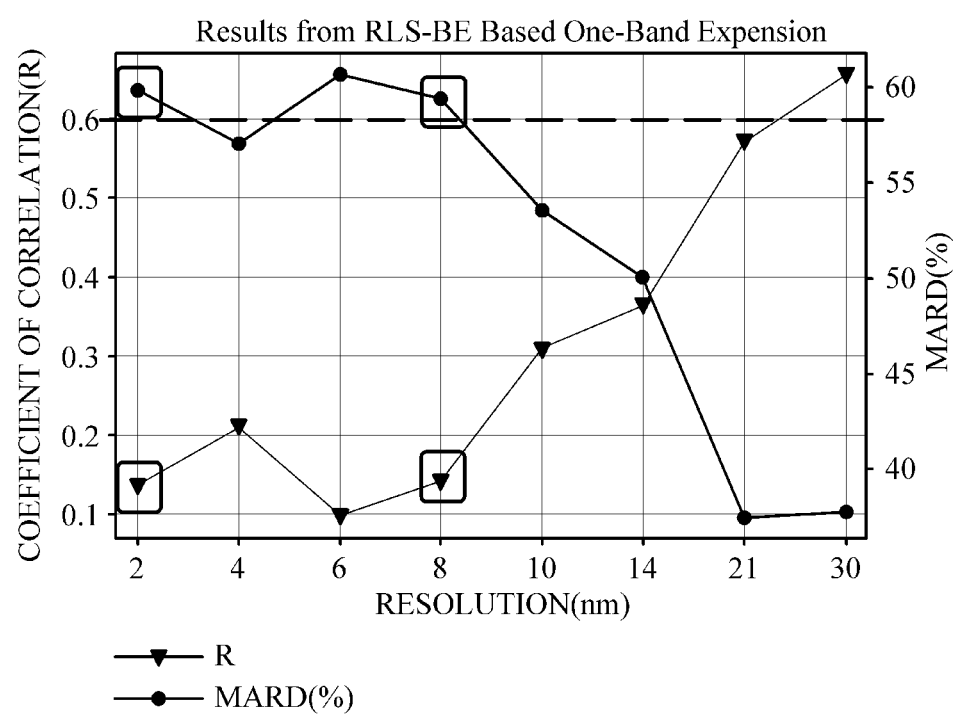

FIGS. 5A and 5B are graphs explaining an example of determining an optimal resolution.

FIG. 5A illustrates a coefficient of correlation between a ground truth for a measurement object and an estimated value which is estimated from a spectrum, and a change in MARD, which are obtained by decreasing a resolution for the key bands determined by forward selection using Random Forest Regression.

For example, when resolution is changed from 2 nm to 30 nm by gradually decreasing the resolution for the determined key bands, a coefficient of correlation between the ground truth and the estimated value is gradually reduced, and MARD is gradually increased.

In this case, the processor 120 may determine an optimal resolution by determining, as a point of trade-off between performance and resolution, a point of minimum resolution where performance is maintained with the correlation coefficient being equal to or greater than 0.6 and the MARD being equal to or lower than 40% based on a predetermined measurement accuracy.

For example, in the case of FIG. 5A, the processor 120 may determine the optimal resolution to be 10 nm, such that performance and accuracy in the determined key bands may be maintained without unnecessarily using a high resolution.

FIG. 5B illustrates a coefficient of correlation between a ground truth for a measurement object and an estimated value which is estimated from a spectrum, and a change in MARD, which are obtained by decreasing a resolution for the key bands determined by backward selection using Partial Least Square Regression (PLSR).

For example, when resolution is changed from 2 nm to 30 nm by gradually decreasing the resolution for the determined key bands, a coefficient of correlation between the ground truth and the estimated value is gradually reduced, and MARD is gradually increased.

In this case, the processor 120 may determine an optimal resolution by determining, as a point of trade-off between performance and resolution, a point of minimum resolution where performance is maintained with the correlation coefficient being equal to or greater than 0.6 and the MARD being equal to or lower than 40% based on a predetermined measurement accuracy.

For example, the processor 120 may determine the optimal resolution to be 8 nm, such that performance and accuracy in the determined key bands may be maintained without unnecessarily using a high resolution.

As described above, in the case where a spectrometer is adapted to use only the key bands determined by the spectrum processing apparatus 100, only some band units obtained by splitting the obtained spectrum are used, such that the spectrometer may be manufactured in a smaller size; and in the case where a spectrometer is adapted to use an optimal resolution for the determined key bands, a signal to noise ratio (SNR) may be improved by the increased light amount as the size of a slit is increased due to a reduced resolution, while the size of the spectrometer is reduced by reducing the size of a grating mirror, which will be described later.

Further, a smaller size of the apparatus and a reduced computation amount may produce gain in the data processing speed, and unnecessary power consumption may be reduced, thereby improving usage performance of a mobile device which is supplied with power from a battery.

For convenience of explanation, the above description is made by using an embodiment where the order of band units is determined based on the feature importance and the correlation coefficient by using Random Forest Regression and Partial Least Square Regression (PLSR), and the key bands are determined by forward selection (FS) or backward selection (BE) of the band units according to the determined order. However, the present disclosure is not limited thereto, and the order of band units may be determined by various machine learning methods. Further, the processor 120 may determine the key bands by using stepwise selection.

Figure 6:
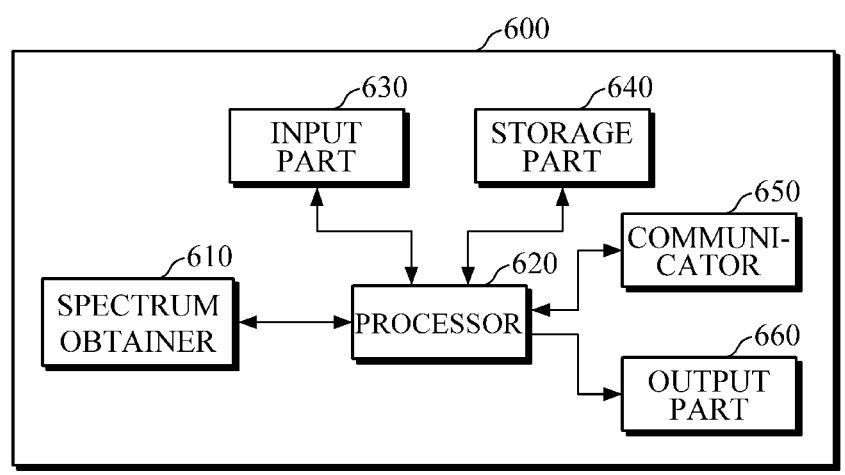
FIG. 6 is a block diagram illustrating a spectrum processing apparatus according to another exemplary embodiment.

FIG. 6 is a block diagram illustrating another example of a spectrum processing apparatus.

Referring to FIG. 6, the spectrum processing apparatus 600 includes a spectrum obtainer 610, a processor 620, an input part (e.g., an input interface) 630, a storage part 640, a communicator (e.g., a communication interface) 650, and an output part (e.g., an output interface) 660.

Here, the spectrum obtainer 610 and the processor 620 basically perform the same functions as the spectrum obtainer 110 and the processor 120 described above with reference to FIG. 1, such that the description below will be made based on details that do not overlap.

The input part 630 may receive a measurement condition, user information, various operation signals, and data required for spectrum processing from a user.

For example, the input part 630 may include a keypad, a dome switch, a touch pad (static pressure/capacitance), a jog wheel, a jog switch, a hardware (H/W) button, and the like. Particularly, the touch pad, which forms a layer structure with a display, may be called a touch screen.

The input part 630 may receive input of user feature information including one of more of occupation, age, gender, weight, and purpose of use of the spectrum measurement apparatus and health information of users.

For example, the processor 620 may set measurement conditions based on the input information, and may classify the users into one or more groups.

The storage part 640 may store programs or commands for operation of the spectrum measurement apparatus 600, and may store data input to and output from the spectrum measurement apparatus 600. For example, the storage part 640 may store user information input through the input part 630, spectrum data obtained by the spectrum obtainer 610, band units obtained by splitting the obtained spectrum, band units determined to be key bands among the band units, and the like.

The storage part 640 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like.

Further, the spectrum measurement apparatus 600 may operate an external storage medium, such as web storage and the like, which performs a storage function of the storage part 640 on the Internet.

The communicator 650 may perform communication with an external device. For example, the communicator 730 may transmit, to the external device, the user information input by a user through the input part 630, the spectrum data obtained by the spectrum obtainer 610, a result of determination of key bands by the processor 620, and an optimal resolution; or the communicator 650 may receive various data, such as user information, spectrum data, measurement condition information, and the like, from the external device.

In this case, the external device may be medical equipment using a spectrum data base (DB) and/or a spectrum processing result, a spectrometer to which the key bands and the optimal resolution is applied, a printer to print out results, or a display device which displays a spectrum quality assessment result.

In addition, examples of the external device may include a digital TV, a desktop computer, a cellular phone, a smartphone, a tablet PC, a laptop computer, a personal digital assistant (PDA), a portable multimedia player (PMP), a navigation, an MP3 player, a digital camera, a wearable device, and the like, but is not limited thereto.

The communicator 650 may communicate with an external device by using Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, ultra-wideband (UWB) communication, Ant+ communication, WIFI communication, Radio Frequency Identification (RFID) communication, 3G communication, 4G communication, 5G communication, and the like. However, this is merely exemplary and the communication part is not limited thereto.

The output part 660 may output, by the control of the processor 620, one or more of the spectrum processing result, the band units, the key bands, and the optimal resolution.

For example, the output part 660 may include a display, a speaker, a vibrator, and the like, through which the output part 660 may output one or more of the spectrum processing result, the band units, the key bands, and the optimal resolution by using at least one of an acoustic method, a visual method, and a tactile method.

Figure 7:
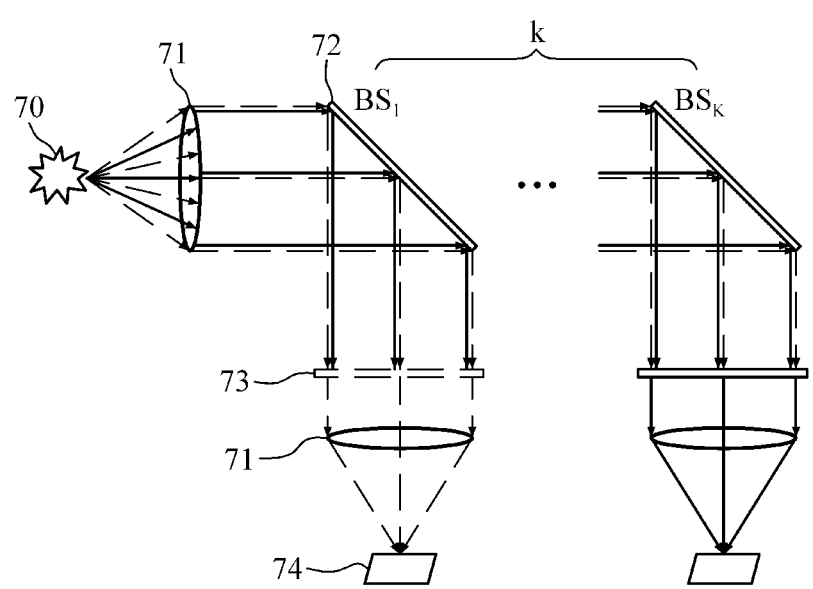
FIG. 7 illustrates an example of an optical structure for determining key bands according to an exemplary embodiment.

FIG. 7 is an exemplary diagram illustrating an example of an optical structure for determining key bands.

Referring to FIGS. 1 and 7, the spectrum obtainers 110 and 610 of the spectrum processing apparatuses 100 and 600 include a light source 70, a lens 71, a beam splitter (BS) 72, a band-pass filter 73, and a detector 74.

The spectrum obtainers 110 and 610 may include a plurality of lenses 71, the beam splitter (BS) 72, the band-pass filter 73, and the detector 74, and may obtain a spectrum of various wavelength bands through the band-pass filter 73 from light transmitted through the beam splitter 72.

For example, in the case of splitting the spectrum into k number of band units, the spectrum obtainers 110 and 610 may include k number of detecting stages including the band-pass filter 74 which passes only the wavelengths of the band units. In this case, the number of the detecting stages may be equal to the number of band units.

In the case where two band units of the wavelength regions of 860 nm and 861 nm are determined to be key bands, if the determined key bands are used in small spectrometer such as a wearable device and/or a mobile device, a light amount may be increased by using only two detecting stages using the band-pass filter which passes only the wavelength regions of 860 nm and 861 nm, thereby reducing the size of a device.

That is, in the case where a spectrometer is adapted to use only the determined key bands, only the band-pass filter, which passes only the wavelength regions of the determined key bands, is used instead of using k number of detecting stages to cover all the wavelength regions, such that an unnecessary optical structure may be simplified, and the spectrometer may become smaller in size.

Figure 8:
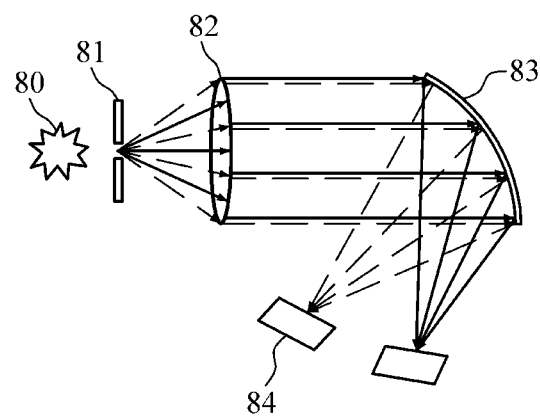
FIG. 8 illustrates an example of an optical structure for determining an optimal resolution according to an exemplary embodiment

FIG. 8 is an exemplary diagram illustrating an example of an optical structure for determining an optimal resolution.

Referring to FIGS. 1 and 8, the spectrum obtainers 110 and 610 include a light source 80, a slit 81, a lens 82, a concave grating mirror 83, and a detector 84. Particularly, the width of the slit 81 may be adjusted, such that resolution of the spectrum processing apparatus may be adjusted by adjusting the width of the slit 81.

For example, the performance of a spectrometer is dependent on resolution, and may be dependent on the number of grating lines of the concave grating mirror. That is, in order to achieve a high resolution, a method of increasing the size of the concave grating mirror or a method of increasing the density of the grating may be used, in which in the former case, the size of the concave grating mirror becomes too large to make the spectrometer smaller in size, and in the latter case, the production cost is increased geometrically.

However, once the optimal resolution is determined by the spectrum processing apparatuses 100 and 600, resolution may be adjusted to the optimal resolution by adjusting the width of the slit, and it is not required to unnecessarily increase the size of the concave grating mirror or the density of the grating, such that the spectrometer may be realized in a smaller size.

As described above, the spectrum processing apparatuses 100 and 600 may use only some key bands determined among a plurality of band units according to measurement conditions, and may determine the optimal resolution for the determined key bands, thereby realizing a small physical optical structure for estimating data from a spectrum.

Figure 9:
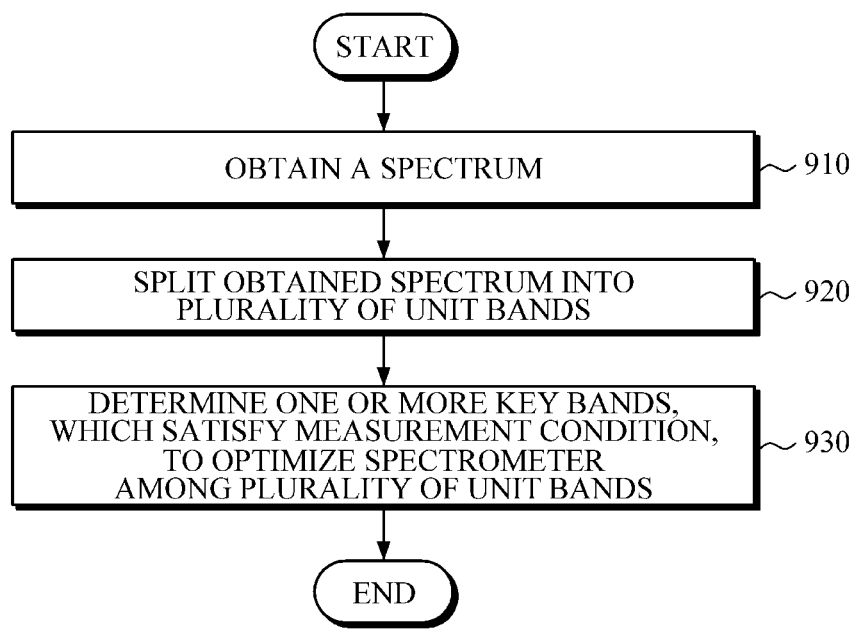
FIG. 9 is a flowchart illustrating a spectrum processing method according to an exemplary embodiment.

FIG. 9 is a flowchart illustrating an example of a spectrum processing method. The spectrum processing method illustrated in FIG. 9 may be performed by the spectrum processing apparatuses 100 and 600 illustrated in FIGS. 1 and 6.

The spectrum processing apparatus 100 may obtain a spectrum in operation 910.

For example, the spectrum processing apparatus 100 may include one or more light sources and a detector, in which the spectrum may be a Raman spectrum using scattered light which is generated when light is emitted from a light source and collides with atoms or molecules in an object.

However, the spectrum is not limited thereto, and the spectrum processing apparatus 100 may obtain an absorption spectrum, a transmission spectrum, or a reflected spectrum, which is measured by emitting near-infrared light or mid-infrared light onto an object.

Upon obtaining the spectrum, the spectrum processing apparatus 100 may split the obtained spectrum into a plurality of band units in operation 920.

For example, the spectrum processing apparatus 100 may split the obtained spectrum into the band units in specific wavelength units.

The spectrum processing apparatus 100 may split all the regions of the obtained spectrum into band units. Further, the spectrum processing apparatus 100 may select only a specific wavelength range required for spectrum analysis, and may split the spectrum in the selected wavelength range into band units. For example, the spectrum processing apparatus 100 may split the wavelength range of 809 nm to 899 nm of the obtained spectrum in the unit of 1 nm, thereby splitting the spectrum into 91 band units.

The spectrum processing apparatus 100 may determine one or more key bands, which satisfy a measurement condition, to optimize a spectrometer among the plurality of band units in operation 930.

Here, the measurement condition may be predetermined according to at least one of a type of a measurement object (e.g., blood pressure, blood sugar, etc.), a minimum or predetermined measurement accuracy, a measurement position of a subject (e.g., a wrist, a finger, etc.), a user group (e.g., an age group and a gender group), a computing power of a processor, and specifications of a measurement apparatus. Further, such measurement condition may be set independently from each other, and may be dependent on other measurement conditions The spectrum processing apparatus 100 may select band units from among the plurality of band units while varying the number of band units, and may repeatedly perform performance evaluation of a spectrometer by using the selected unit bands; and may determine, as key bands, a predetermined number of unit bands which satisfy the performance evaluation of the spectrometer.

For example, the spectrum processing apparatus 100 may select a predetermined number of unit bands from among the plurality of unit bands. Upon selecting the unit bands, the spectrum processing apparatus 100 may repeatedly perform performance evaluation by using the selected unit bands.

For example, the spectrum processing apparatus 100 may determine whether a result of performance evaluation satisfies a measurement condition; and if the measurement condition is satisfied based on the determination, the spectrum processing apparatus 100 may change a predetermined number of the band units, and may select the band units again. By contrast, if the measurement condition is not satisfied based on the determination, the spectrum processing apparatus 100 may determine the number of band units before change to be key bands.

That is, by repeatedly performing performance evaluation using a predetermined number of band units while varying the number of band units until the measurement condition is not satisfied, the spectrum processing apparatus 100 may determine a predetermined number of band units to be key bands.

For example, the spectrum processing apparatus 100 may extract features of the band units, and may determine a rank of each band unit according to feature importance of each unit band. That is, the spectrum processing apparatus 100 may determine the rank of each band unit in order of the calculated feature importance.

For example, in proceeding to selecting a number of band units in response to a result of the performance evaluation satisfying a measurement condition, the spectrum processing apparatus 100 may determine the number of band units to be changed by determining the rank of each band unit according to the importance of band units, and by forward selection of band units which are ranked high based on the determined rank of each unit band.

In this case, the spectrum processing apparatus 100 may determine the rank of the band units by using Random forest regression.

That is, the spectrum processing apparatus 100 may determine the rank of the band units by using Random forest regression (RFR), in which a coefficient of correlation between a ground truth for a measurement object and an estimated value which is estimated from the selected band units, and a change in Mean Absolute Relative Difference (MARD), by varying the number of all the band units in the wavelength regions until one band unit remains.

Upon calculating the correlation coefficient and the change in MARD, the spectrum processing apparatus 100 may determine a trade-off between the performance and size of a spectrometer and reliability of the estimated value. For example, by determining, as key bands, two band units having the highest importance, a trade-off between the performance and size of a spectrometer and reliability of the estimated value may be obtained, such that the spectrum processing apparatus 100 may determine the two band units to be key bands.

Further, in proceeding to selecting a number of band units in response to a result of the performance evaluation satisfying a measurement condition, the spectrum processing apparatus 100 may determine the rank of each band unit based on a correlation between the band units, and may determine the number of band units to be changed by backward elimination of band units in a lower rank.

For example, the spectrum processing apparatus 100 may determine the rank of each band unit by using Partial Least Square Regression (PLSR).

That is, the spectrum processing apparatus 100 may determine the rank of each band unit by backward elimination using Partial Least Square Regression (PLSR), and may calculate a coefficient of correlation between a ground truth for a measurement object and an estimated value which is estimated from the selected band units, and a change in Mean Absolute Relative Difference (MARD).

Upon calculating the correlation coefficient and the change in MARD, the spectrum processing apparatus 100 may determine a trade-off between the performance and size of a spectrometer and reliability of the estimated value. For example, by determining, as key bands, two band units having the highest correlation, a trade-off between performance, size, and reliability may be obtained, such that the spectrum processing apparatus 100 may determine the two band units to be key bands.

As described above, in the case where a spectrometer is adapted to use only the key bands determined by the spectrum processing apparatus 100, only some of the band units obtained by splitting the obtained spectrum are used, such that the spectrometer may be manufactured in a smaller size.

Figure 10:
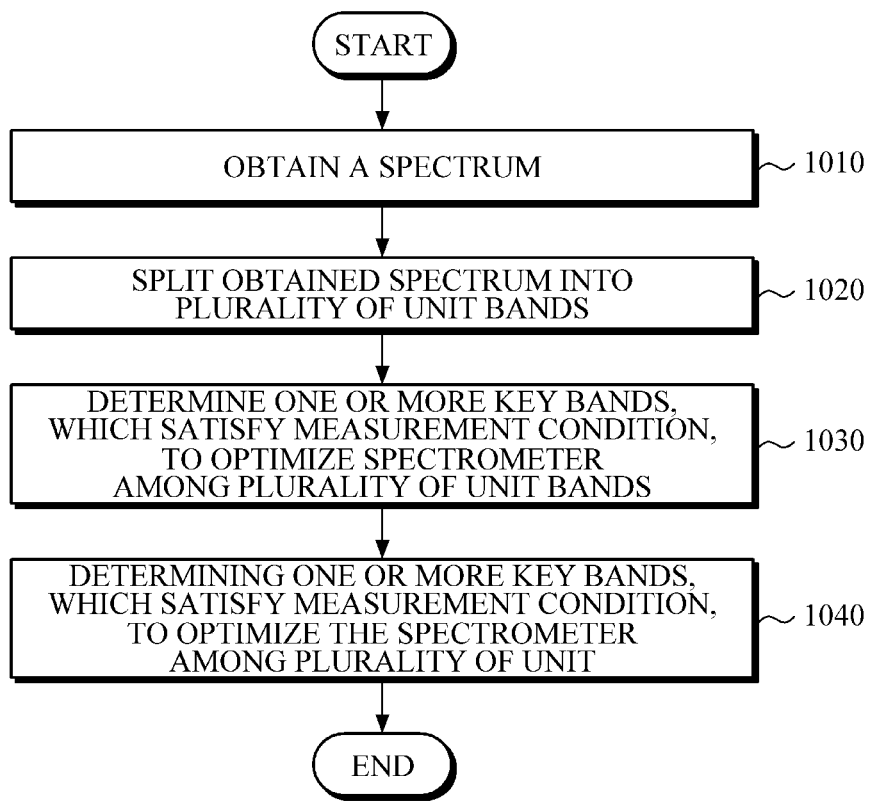
FIG. 10 is a flowchart illustrating a spectrum processing method according to another exemplary embodiment.

FIG. 10 is a flowchart illustrating another example of a spectrum processing method. The spectrum processing method of FIG. 10 may be performed by the spectrum processing apparatuses 100 and 600 illustrated in FIGS. 1 and 6.

Further, obtaining a spectrum in 1010, splitting the obtained spectrum into a plurality of band units in 1020, and determining one or more key bands, which satisfy a measurement condition, to optimize the spectrometer among the plurality of band units in 1030, may be generally performed in the same manner as the operations 910, 920, and 930 of FIG. 9, such that description below will be made based on details that do not overlap.

Upon determining the key bands, the spectrum processing apparatus 100 may determine an optimal resolution of the spectrometer, which satisfies a measurement condition, while adjusting a resolution for the determined key bands in 1040.

Here, the optimal resolution may be a resolution of a spectrometer that satisfies a measurement condition, and may be a minimum resolution for the key bands determined according to the measurement condition.

That is, when the spectrum processing apparatus 100 changes resolution from 2 nm and 30 nm by gradually decreasing the resolution for the determined key bands, a coefficient of correlation between the ground truth and the estimated value shows a tendency to be gradually reduced, and MARD shows a tendency to be gradually increased.

In this case, the spectrum processing apparatus 100 may determine an optimal resolution by determining, as a point of trade-off between performance and resolution, a point of minimum resolution where performance is maintained with the correlation coefficient being equal to or greater than 0.6 and the MARD being equal to or lower than 40% based on a predetermined measurement accuracy.

For example, the spectrum processing apparatus 100 may set a resolution for the determined key bands, and may perform performance evaluation of the spectrometer based on the set resolution.

In this case, based on a result of performance evaluation of the spectrometer, if a measurement condition is satisfied, the spectrum processing apparatus 100 may perform again performance evaluation by adjusting resolution, and if a measurement condition is not satisfied, the spectrum processing apparatus 100 may determine resolution before adjustment to be an optimal resolution.

That is, the spectrum processing apparatus 100 may determine whether a measurement condition is satisfied by adjusting resolution for the determined key bands, and may determine resolution, which satisfies the measurement condition, to be an optimal resolution for the determined key bands.

As described above, in the case where the spectrum processing apparatus 100 determines the optimal resolution for the determined key bands, performance and accuracy in the determined key bands may be maintained without using an unnecessarily high resolution.

In the case where a spectrometer is adapted to use the optimal resolution for the key bands determined by the spectrum processing apparatus 100, a signal to noise ratio (SNR) may be improved by the increased light amount as the size of a slit is increased due to a reduced resolution, while the size of the spectrometer is reduced by reducing the size of a grating mirror.

While not restricted thereto, an exemplary embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A spectrum processing apparatus, comprising:
    a spectrometer configured to obtain an optical spectrum from a light that is scattered or reflected from a subject; and
    a processor configured to split the optical spectrum into a plurality of bands, determine, based on a predetermined measurement accuracy for measuring a biosignal from the light, one or more key bands from the plurality of bands, and obtain the biosignal from the determined key bands,
    wherein upon determining the key bands, the processor determines a resolution of the spectrometer that satisfies the predetermined measurement accuracy by adjusting a resolution for the determined key bands.

2. The spectrum processing apparatus of claim 1, wherein the processor is further configured to determine the key bands based on at least one of a type of a measurement object, a measurement position of the subject, an age group to which the subject belongs, a gender group to which the subject belongs, and a computing power of a bio-information measurement apparatus including the spectrometer.

3. The spectrum processing apparatus of claim 1, wherein the processor is further configured to determine a number of the key bands to be selected from the plurality of bands by selecting bands from the plurality of bands while varying a number of the selected bands, and by repeatedly performing performance evaluation of the spectrometer by using the selected bands.

4. The spectrum processing apparatus of claim 3, wherein the processor is further configured to determine a rank of each of the plurality of bands, and determine, among the plurality of bands, a number of candidate bands to be changed by performing forward selection on one or more of the plurality of bands having a rank higher than a first predetermined rank, based on the determined rank of each of the plurality of bands.

5. The spectrum processing apparatus of claim 4, wherein the processor is further configured to determine the rank of each of the plurality of bands based on Random Forest Regression.

6. The spectrum processing apparatus of claim 3, wherein the processor is further configured to determine a number of candidate bands to be changed, by determining a rank of each of the plurality of bands according to a correlation between the plurality of bands, and by performing backward elimination on one or more of the plurality of bands having a rank lower than a second predetermined rank.

7. The spectrum processing apparatus of claim 6, wherein the processor is further configured to determine the rank of each of the plurality of bands based on Partial Least Square Regression.

8. The spectrum processing apparatus of claim 1, further comprising a communicator configured to obtain a spectrum from an external spectrum detection apparatus.

9. The spectrum processing apparatus of claim 1, wherein the optical spectrum is a Raman spectrum.

10. A spectrum processing method, comprising:
obtaining an optical spectrum from a light that is scattered or reflected from a subject;
splitting the optical spectrum into a plurality of bands;
determining one or more key bands from the plurality of bands based on a predetermined measurement accuracy for measuring a biosignal from the light; and
obtaining the biosignal from the determined key bands,
wherein the spectrum processing method is performed by a spectrometer, and the spectrum processing method further comprises, upon determining the key bands, determining a resolution of the spectrometer that satisfies the predetermined measurement accuracy by using the determined key bands.

11. The spectrum processing method of claim 10, wherein the determining one or more key bands comprising determining the one or more key bands further based on at least one of a type of a measurement object, a measurement position of the subject, an age group to which the subject belongs, a gender group to which the subject belongs, and a computing power of the spectrometer that performs the spectrum processing method.

12. The spectrum processing method of claim 10, wherein the determining the key bands comprises:
selecting a predetermined number of candidate bands from the plurality of bands;
evaluating performance of the spectrometer that performs the spectrum processing method by using the selected candidate bands;
determining whether a result of evaluating the spectrometer satisfies the predetermined measurement accuracy;
in response to the result of evaluating the performance of the spectrometer satisfying the predetermined measurement accuracy, changing the predetermined number of candidate bands and selecting the candidate bands as the key bands; and
in response to the result of evaluating the performance of the spectrometer not satisfying the predetermined measurement accuracy, determining the predetermined number of candidate bands to be the key bands.

13. The spectrum processing method of claim 12, wherein the selecting the candidate bands comprises:
determining a rank of each of the plurality of bands; and
determining, among the plurality of bands, a number of the candidate bands to be changed by performing forward selection on one or more of the plurality of bands having a rank higher than a first predetermined rank based on the determined rank of each of the plurality of bands.

14. The spectrum processing method of claim 13, wherein the determining the rank of each of the plurality of bands comprises determining the rank based on Random Forest Regression.

15. The spectrum processing method of claim 12, wherein the selecting the candidate bands comprises:
determining a rank of each of the plurality of bands according to a correlation between the plurality of bands; and
determining a number of the candidate bands to be changed by performing backward elimination on one or more of the plurality of bands having a rank lower than a second predetermined rank based on the determined rank of each of the plurality of bands.

16. The spectrum processing method of claim 15, wherein the determining the rank of each of the plurality of bands comprises determining the rank based on Partial Least Square Regression.

17. The spectrum processing method of claim 10, wherein the determining the resolution comprises:
setting the resolution for the determined key bands;
evaluating performance of the spectrometer based on the set resolution;
in response to a result of evaluating the performance of the spectrometer satisfying the predetermined measurement accuracy, adjusting the resolution for the determined key bands and evaluating the performance of the spectrometer; and
in response to a result of evaluating the performance of the spectrometer not satisfying the predetermined measurement accuracy, determining the resolution that is set for the determined key bands before adjustment, to be the resolution of the spectrometer.

18. The spectrum processing method of claim 10, wherein the obtaining the optical spectrum comprises obtaining the optical spectrum from an external spectrum detection apparatus through a communication module.

* * * * *